United States Patent
Michot et al.

(10) Patent No.: US 6,296,973 B1
(45) Date of Patent: Oct. 2, 2001

(54) SOLVENTS AND NOVEL ELECTROLYTIC COMPOSITIONS HAVING A LARGE RANGE OF STABILITY AND HIGH CONDUCTIVITY

(75) Inventors: Christophe Michot, Grenoble (FR); Dany Brouillette; Daniel Baril, both of Montreal (CA); Jean-Yves Bergeron, Longueuil (CA); Michel Armand, Montreal (CA)

(73) Assignees: Hydro - Quebec; ACEP Inc, both of Montreal (CA); Centre National de la Rechecch Scientifique, Paris (FR); Universite de Montreal, Montreal (CA)

( * ) Notice: Subject to any disclaimer, the term of this patent is extended or adjusted under 35 U.S.C. 154(b) by 0 days.

(21) Appl. No.: 09/151,599

(22) Filed: Sep. 11, 1998

(30) Foreign Application Priority Data

Sep. 11, 1997 (CA) .................................................. 2215849

(51) Int. Cl.[7] ...................................................... H01M 6/14
(52) U.S. Cl. ........................ 429/300; 429/315; 429/317; 429/322; 429/330; 252/62.2
(58) Field of Search .................................. 429/300, 315, 429/317, 322, 330; 252/62.2

(56) References Cited

U.S. PATENT DOCUMENTS

| | | | |
|---|---|---|---|
| 4,250,092 | 2/1981 | Kaifjez | 260/239 |
| 4,303,748 * | 12/1981 | Armand et al. | 429/192 |
| 4,816,372 | 3/1989 | Schenk et al. | 430/203 |
| 4,851,307 | 7/1989 | Armand et al. | 429/192 |
| 4,899,249 * | 2/1990 | Reilly et al. | 361/317 |
| 5,063,124 | 11/1991 | Gauthier et al. | 429/192 |
| 5,723,664 | 3/1998 | Sakaguchi et al. | 564/82 |

FOREIGN PATENT DOCUMENTS

| | | |
|---|---|---|
| 876 201 | 9/1979 | (BE) . |
| 2 300 084 | 7/1974 | (DE) . |
| 36 32 737 | 3/1988 | (DE) . |
| 0 125 093 | 11/1984 | (EP) . |
| 0 126 558 | 11/1984 | (EP) . |
| 0 339 284 | 11/1989 | (EP) . |
| 0 850 920 * | 7/1998 | (EP) . |

OTHER PUBLICATIONS

Chemical Abstracts, vol. 72, No. 13, AN 72:66338, S.P. Von Halasz, et al., "Preparation of New Aminosulfur Monofluoride Imides and Aminosulfur Oxide Monofluoride Imides and The Structure of Aminosulfur Oxide Trifluorides", 1970.

P. Sartori, et al., Meeting Abstracts, vol. 97–1, p. 1148, "Recent Development in Electrochemical Fluorination (Simons Process)", May 4–9, 1997.

* cited by examiner

*Primary Examiner*—Laura Weiner
(74) *Attorney, Agent, or Firm*—Oblon, Spivak, McClelland, Maier & Neustadt, P.C.

(57) ABSTRACT

The present invention is concerned with novel polar solvents and novel electrolytic compositions comprising such solvents, and having a high range of stability, as required for applications in the field of electrochemistry. The present solvents have a highly polar amide function, and preferably combine with a salt soluble in the solvent and having an anion with a delocalized charge, and at least one polymer, to form an electrolytic composition.

11 Claims, No Drawings

SOLVENTS AND NOVEL ELECTROLYTIC COMPOSITIONS HAVING A LARGE RANGE OF STABILITY AND HIGH CONDUCTIVITY

FIELD OF INVENTION

The invention concerns new polar solvents and new electrolytic compositions comprising the same, and having a large range of stability, as required for applications in the field of electrochemistry.

BACKGROUND OF THE INVENTION

Polar aprotic solvents such as cyclic or linear carbonates, or ethers used alone or in mixtures, are known in various electrolytic compositions. The stability of these products towards highly negative potentials, close to those of alkaline metals, or highly positive ($\geq 4$V with respect to $Li^+/Li°$), are not satisfactory, and lithium batteries containing electrolytes obtained from the dissolution of a lithium salt in these solvents create serious safety problems. Products of the amide type, whether linear or cyclic, such as dimethylformamide or N-methylpyrrolidinone, possess excellent properties as solvents, but are oxidized at potentials that are still lower, in the order of 3.7 V with respect to $Li^+/Li°$.

Numerous materials of positive electrodes, such as mixed oxides of transition metals and lithium work under potentials near 4 V with respect to $Li^+/Li°$ and therefore require electrolyte stabilities significantly higher than that value. For example, products like $Li_{1-y}Co_{1-x-z}Ni_xAl_yO_2$ wherein $x+y \leq 1$ and $z \leq 0,3$); manganese spinels $Li_{1-\alpha}Mn_{2-x}M_xO_4.Li_{1-\alpha}Co_{1-x-y}Ni_xAl_y$ wherein $0 \leq x+y \leq 1$; $0 \leq y \leq 0,3$; $0 \leq \alpha \leq 1$ and M=Li, Mg, Al, Cr, Ni, Co, Cu, Ni, Fe.

U.S. Pat. Nos. 4,851,307 and 5,063,124 describe electrolytes comprising a salt, a solvating polymer and an aprotic sulfamide of the general formula

wherein $R^1$, $R^2$, $R^3$ and $R^4$, the same or different, are independently selected from $C_{1-10}$alkyl or $C_{1-10}$oxaalkyl. An example of the product of that group is the tetraethylfulfamide ($R^1=R^2=R^3=R^4=C_2H_5$). These materials have increased stability towards reducing or basic agents present and having potentials near those of alkaline metals. However, they are oxidized at potentials between 3.8 and 4V with respect to $Li^+/Li°$.

EP 0 339 284 discloses dielectric and insulating compounds like perfluoro-acylamides or perfluoro-sulfonamides $R_FCONA^1A^2$ and $R_FSO_2NA^1A^2$, wherein $A^1$ and $A^2$ are alkyl groups. The proposed use of these products in capacitors implies that the materials are not conductive and that the impurities and inevitable contaminants, particularly ionic products, are not inducing significant conductivity.

The publication of Sartori et al. in an abstract of a meeting of the Electrochemical Society, Volume 97-1, May 1997, describes certain sulfonamides that could be used as electrolytes in a battery or in an energy storage system.

SUMMARY OF THE INVENTION

In accordance with the present invention, there is provided novel polar solvents and novel electrolytic compositions comprising the same and having a high degree of stability, as required for applications in the field of electrochemistry. More specifically, the solvents of the present invention are of the general formula

wherein
X=C or SO;
Z=O, $NSO_2NR_3R_4$ or NCN;
$R^1$ $R^2$ are the same or different and are $C_{1-18}$alkyl, $C_{1-18}$ oxaalkyl, $C_{1-18}$ alkylene or $C_{1-18}$oxaalkylene;
$R^3$ to $R^6$ are the same or different and are $C_{1-18}$alkyl or $C_{1-18}$ oxaalkyl;
$R^7$ is $R_F$, $R_FCH_2O$—, $(R_F)_2CHO$—, $(R_FCH_2)_2N$— or $NR^5R^6$;
$R_F$ is fluorine, $C_{1-4}$alkyl, $C_{1-4}$oxaalkyl or $C_{1-4}$azaalkyl wherein the alkyl chain is preferably essentially fluorinated and partly chlorinated,
with the provisos that:
1) if Z=O, then $R_F$ is not $C_{1-4}$alkyl; and
2) if Z=O and X=SO, then $R^5$ or $R^6$ is not $C_{1-4}$alkyl or $C_{1-4}$oxaalkyl.

The expression "essentially fluorinated" means that the degree of fluorination in the chain is sufficient to provide properties similar to those obtained with a chain entirely perfluorated, such as a hydrophobic character and properties of attracting electrons. Preferably, at least half of the hydrogen atoms of the chain are replaced by fluorine atoms. The expression "partially chlorinated" means that within the essentially fluorinated products, the hydrogen atoms remaining are at least partially replaced with chlorine atoms.

DETAILED DESCRIPTION OF THE INVENTION

In the present invention, materials with a highly polar amide function are used for preparing electrolytic compositions useful for electrochemical applications. It has unexpectedly been found that groups strongly attracting electrons, when combined with the amide function, allow the maintenance of solubilizing power towards ionic products, particularly those having a highly delocalized anionic charge, and thus inducing high ionic conductivities. By adding a polar polymer to these compositions, there is obtained electrolytes with mechanical properties allowing the fabrication of films for use in electrochemical devices, and increasing the security when in operation. Depending on the amount of polar solvent and polymer in the electrolytic compositions, the consistency thereof can be adjusted to a gel or a plasticized polymer. Further, the polymers can be reticulated to improve mechanical properties.

The electrolytic compositions of the present invention have higher stability when compared to materials of the prior art, particularly at very anodic potentials, especially those exceeding 4 V with respect to $Li^+/Li°$.

Preferred low energy reticular salts that are soluble in the polar solvents of the present invention to form conductive solutions comprise those having a delocalized charge, such as $I^-$, $ClO_4^-$, $BF_4^-$, $PF_6^-$, $AsF_6^-$, $SbF_6^-$, $R_FSO_3^-$, $XSO_2NSO_2X'^-$, $(XSO_2)(X'SO_2)(Y)C^-$ and mixtures thereof, wherein
X and X' is $R_F$, $R_FCH_2O$—, $(R_F)_2CHO$—, $(R_FCH_2)_2N$—, $R^8$, $R^9R^{10}N$—, with the proviso that at least one X or X' is $R_F$, $R_FCH_2O$—, $(R_F)_2CHO$—, $(R_FCH_2)_2N$—;
Y=$R_F$, $R_FSO_2$ or CN;
$R_F$ is as defined above; and
$R^8$ to $R^{10}$ are the same or different, and are $C_{1-18}$alkyl or —$C_{1-18}$ oxaalkyl.

$R_F$ and $R^8$–$R^{10}$ can be part of a molecular chain. Also preferred are anions derived from 4,5-dicyano-1,2,3-triazole, 3,5-bis($R_F$)-1,2,4-triazole, tricyanomethane, pentacyanocyclopentadiene and pentakis(trifluoromethyl) cyclopentadiene and anions derived from cyanamide and malononitrile, i.e., $R_FSO_2NCN^-$, $C(CN)_3^-$, $R_FSO_2C(CN)_2^-$.

Preferred cations comprise those derived from alkaline metals, more preferably lithium, alkaline earth metals, and organic cations of the "onium" type, such as ammonium, imidazolium, sulphonium, phosphonium and oxonium.

With respect to the electrolytic compositions of the present invention, they include those containing at least one polar solvent as defined above in combination with one or more polar molecules acting as a co-solvent. Such other polar molecules include solvents capable of forming compatible mixtures, such as dialkyl ethers of ethylene glycol, diethylene glycol, triethylene glycol, polyethylene glycols preferably having a mass of from 400 to 2000; or esters, preferably carbonic acid esters, whether linear or cyclic, such as dimethylcarbonate, methylethylcarbonate, diethylcarbonate, ethylene carbonate, propylene carbonate, or esters such as γ-butyrolactone, nitriles such as glutaronitrile, or 1,2,6-tricyanohexane. These other polar molecules, or co-solvent, can be added alone or in mixtures to the solvent of the present invention. An example of the preferred mixture is ethylene carbonate with a dialkyl ether.

The present invention further includes solid electrolytes obtained by the addition of the polymer to a solvent or solvent-co-solvent mixture containing at least one salt as defined above in solution. The amount of polymer can be selected so that the solvent acts as a plasticizing agent of the polymer, i.e. in concentration of 3 to 30% by weight, preferably between 10 and 25% by weight. Preferred polymers for such compositions are those with monomer units containing solvating units, such as those derived from ethylene oxide, propylene oxide, epichlorohydrine, epifluorohydrine, trifluoroepoxypropane, etc. To obtain a gel, the amount of solvent and salt in the composition should be between 30 and 95% by weight, preferably between 40 and 70%. In addition to the polymers listed above, those containing units derived from acrylonitrile, methylmethacrylate, vinylidene fluoride, N-vinylpyrolidinone are also preferred, and can be either homo- or copolymers, such as vinylidene fluoride and hexafluoropropene copolymers. A copolymer containing from 5 to 30% molar of hexafluoropropene is particularly preferred. In a variation, the polymers are polyelectrolytes incorporating anions with a delocalized charge in the macromolecular chain. In such conditions, negative charges are immobilized and only positive counter-charges participate in the ionic conduction process.

The present electrolytic compositions can be used wherever a high stability is required, particularly when oxidation or highly positive potentials are present. A good example is an electrochemical generator wherein it is advantageous to have a high electromotive force, particularly in generators containing lithium ions. In such systems, the negative electrode comprises metallic lithium, one of its alloys, a carbon derivative, preferably petrolium coke or graphite, an oxide with a low potential of intercalation such as titanium spinels $Li_{2x+1+3y}Ti_{x+5}O_{12}$ ($x \geq 0$ and $y \leq 1$), a double nitride of a transition metal and lithium such as $Li_{3-x}Co_xN$, or having an antifluorite type structure such as $Li_3FeN_2$ or $Li_7MnN_4$.

The materials for the positive electrode comprise intercalation compounds, polysulfides or oxocarbones. Intercalation compounds include vanadium oxide, and preferably those with the formula $VO_x$ wherein $2 \leq x \leq 2.5$; $LiV_3O_8$; cobalt and lithium mixed oxides of the general formula $Li_{1-\alpha}Co_{1-x-y}Ni_xAl_y$ wherein $0 \leq x+y \leq 1$; $0 \leq y \leq 0,3$; $0 \leq \alpha \leq 1$; partly substituted manganese spinels of the general formula $Li_{1-\alpha}Mn_{2-z}M_zO_4$ wherein $0 \leq z \leq 1$ and M=Li, Mg, Al, Cr, Ni, Co, Cu, Ni, Fe; and double phosphates of the olivine or Nasicon structure such as $Li_{1-\alpha}Fe_{1-x}Mn_xPO_4$, $Li_{1-\alpha+2x}Fe_2P_{1-x}S_xO_4$, wherein $x \geq 0$ and $\alpha \leq 1$. Oxocarbones electrode materials are preferably rhodizonic acid salts; polydisulfides including derivatives resulting from the oxidation of dimercaptoethane, 2,5-dimercapto-1,3,4-thiadiazole, 2,5-dimercapto-1,3,4-oxaadiazole, and 1,2-dimercaptocyclobutene-3,4-dione.

Electrochemical generators using the present electrolytic compositions preferably contain solid electrolytes, either plasticized or gelled. In a preferred embodiment of the invention, at least one of the electrodes is a composite comprising the electrode materials in a mixture with the electrolytic composition and carbon such as Shawinigan® black, Ketjenblack®, or graphite.

Another application of the invention is that of supercapacitors wherein at least one electrode comprises high surface area carbon, and the electrical energy is stored as a result of the capacity of the double layer between the carbonated material and the electrolyte. In a preferred embodiment, the two electrodes are symmetrically built with carbon having high surface area, and this material is mixed with the electrolyte to form a composite. Another possibility is to use the electrode material containing at least one polymer having conjugated double bonds. In a preferred embodiment, the conjugated polymer may have three degrees of oxidation, obtained by reduction ("n" doping) concomitant to an injection of electrons and cations, or by oxidation ("p" doping) concomitant to an electron extraction and anion injections, from the neutral form. Polymers comprising phenyl-3-thiophene, and particularly poly(4-fluorophenyl-3-thiophene) are preferred.

The following examples are provided to illustrate the preferred embodiments of the present invention, and should not be construed as limiting its scope.

EXAMPLE 1

Trifluoroethanol (18.2 mL, 25 mml) dissolved in 100 mL of ether are added to 7 g of sodium hydride. When no more hydrogen gas evolves, the solution is centrifuged and the supernatant clear liquid is added at 0° C. to 35 μg (25 mml) of dimethysulfamoyl chloride dissolved in 100 mL of dry ether under stirring. A white precipitate of NaCl forms and the reaction is completed in two hours. The slurry is filtered and the ether stripped in a rotary evaporator. The residue is diluted with 50 ml of dichloromethane and washed with 10% HCl in water. The organic layer is separated, dried with anhydrous magnesium sulfate. The corresponding trifluoethyl-N,N dimethylsulfamate is distilled under reduced pressure. RMN: $^{19}$F: triplet δ=74.7 ppm, $J_{HF}$=8.1 Hz; $^1$H: quartet δ=4.66 (2H), singlet δ=3.6 (6H). The conductivity of the lithium salts of the bis (trifluoromethanesulfonimide) $(CF_3SO_2)_2NLi$ in solution in this solvent is provided in Table 1 with respect to several concentrations.

TABLE 1

| molality (mol · kg$^{-1}$) | conductivity $k_{sp}$ (S · cm$^{-1}$) |
|---|---|
| 0.265 | 0.634 |
| 0.506 | 0.922 |
| 0.898 | 1.025 |
| 1.160 | 0.796 |

The range of electrochemical stability is measured by cyclic voltametry on a platinum microelectrode (15 μm diameter) for anodic potentials, and nickel for cathodic potentials. The stability range is from 0 to 5.2 V vs. Li$^+$/Li°.

The variation of conductivity with respect to the temperature is found is Table 2 for a concentration of 0.898 mol.kg$^{-1}$.

TABLE 2

| T (° C.) | K$_{sp}$ (S · cm$^{-1}$) |
|---|---|
| 14.90 | 0.753 |
| 14.92 | 0.7550 |
| 19.93 | 0.882 |
| 25.11 | 1.030 |
| 30.29 | 1.203 |
| 35.39 | 1.415 |
| 40.81 | 1.657 |

EXAMPLE 2

107.4 mL of dimnethylsulfamoyl chloride are heated under reflux and nitrogen atmosphere with 70 g of potassium fluoride and 10 mL of water. The mixture is cooled and extracted with dichloromethane, dried with magnesium sulphate, and distilled. The compound obtained, (CH$_3$)$_2$NSO$_2$F, has a dielectric constant greater than 30. The range of stability, as determined by cyclic voltanietry, is 5 V vs. Li$^+$/Li°. The lithium salt of the fluorosulfonimide (FSO$_2$)$_2$NLi is soluble in this medium, and its conductivity at 25° C. is greater than 1 mScm$^{-1}$ for concentrations between 0.5 and 1 mole.kg$^{-1}$.

EXAMPLE 3

1.6 g of sodium hydride are added to 6.3 mL of 1,1,1,-3,3,3,-hexafluoropropanol dissolved in 25 ml of anhydrous ether. When no more hydrogen gas evolves, the solution is centrifuged, and 8.6 µg (60 mml) of dimethylsulfamoyl chloride dissolved in 25 mL of dry ether are added to the supernatant liquid under agitation at a temperature of 0° C. A white precipitate of sodium chloride is then formed et the reaction is completed after 2 hours. The slurry is filtered and the ether is evaporated with a rotary evaporator. The residue is placed in 20 mL of dichloromethane and washed with an aqueous solution of 10% hydrochloric acid. The organic phase is separated and dried with anhydrous magnesium sulphate. The hexafluoropropyle N,N-dimethylsulfamate is obtained by evaporating the dichloromethane and distilled under reduced pressure. The compound has a dielectric constant greater than 20, and the conductivity of solutions of salts of bis(trifluoromethanesulfonimide) (NC$_2$H$_5$)$_4$(CF$_3$SO$_2$)$_2$N in this solvent are between 5×10$^{-4}$ and 2×10$^{-3}$ Scm$^{-1}$ at 25° C. in concentrations varying from 0.2 to 1 mole.kg$^{-1}$.

EXAMPLE 4

4.2 g of cyanamide and 11.22 g of diazabicyclo 2,2,2-octane (DABCO) are added to 15.76 g of ethylmethylsulfamoyl chloride dissolved in 100 mL of tetrahydrofuran. After agitating the mixture at room temperature for 8 hours, 13 g of oxalyl chloride dissolved in 40 mL of anhydrous tetrahydrofuiran are added dropwise. After gas emissions have stopped (CO and CO$_2$), the DABCO chlorohydrate is filtered and remaining TIF is evaporated under reduced pressure. The solid is then placed in 50 mL of acetonitrile to which is added 12.2 g of ethylmethylamine at 0° C. The ethylmethylammonium chloride thus obtained is separated and the solvent is evaporated under reduced pressure. The polar product

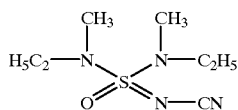

The polar product is solubilized in dichloromethane, and washed with water containing 2% hydrochloric acid, and subsequently 5% sodium bicarbonate. Following removal of dichloromethane, the compound is distilled under reduced pressure. This product can be used as a solvent for delocalized anions salts, particularly perfluorinated imides.

EXAMPLE 5

33 g of 1,1-dimethylsulfamde (CH$_3$)$_2$SO$_2$NH$_2$ and 6 g of caustic soda in 200 mL of water are heated to reflux for 2 hours. The reaction product, the sodium salt of bis (dimethylarninosulfonimide), i.e., Na[N(SO$_2$N(CH$_3$)$_2$)], is obtained by evaporation of the water and recristallisation in ethanol. 25 g of this salt suspended in 100 mL of anhydrous are reacted with 9 mL of oxalyl chloride. At then end of the reaction, i.e., no more gas emissions, the slurry is cooled to 0° C. and 20.7 mL of diethylamine dissolved in 50 mL of acétonitrile are added. The mixture is then agitated for 4 hours at room temperature, and subsequently filtered. Any remaining acetonitrile is removed under reduced pressure. The liquid obtained is solubilized in dicliloromethane and washed with water containing 2% hydrochloric acid, and subsequently 5% of sodium bicarbonate. The solution is passed through an alumina column and the dichloromethane is evaporated under reduced pressure. The polar solvent

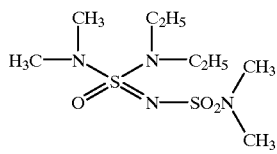

is kept anhydrous by adding lithium hydride.

EXAMPLE 6

An electrochemical generator comprising a negative electrode of lithium of 25 Jim on a nickel support of 10 µm, a positive electrode composite containing 78% by weight of vanadium oxide V$_2$O$_5$, 8% of carbon black (Ketjenblack®) and 14% of a vinylidene fluoride—hexafluoropropene copolymer on a nickel collector (10 µm) has been prepared. The positive electrode capacity thus obtained by spreading from a cyclohexanone suspension, is 2.8 mAh/cm$^2$. The electrolyte comprises a solution of 0.15 M.kg$^{-1}$ of Li(CF$_3$SO$_2$)$_2$N in the polar compound of Example 1 in a polypropylene porous separator of the Celgard® type. The generator was cycled over 150 cycles between 1.6 et 3.4V at C/3.7 while maintaining a ratio of charge and discharges capacities equal to 1 and a use rate of >75% over 30 cycles. The ohmic drop remained between 20 and 120 mV.

EXAMPLE 7

An electrochemical generator of the "rocking chair" type was prepared with 2 composite electrodes similar to those of Example 6. Lithium and titanium spinel Li$_4$Ti$_5$O$_2$ was used as the negative electrode, to give a surface capacity of 2.6 mAh.cm$^{-2}$. Lithium cobaltite was used for the positive electrode, to give a surface capacity of 2.4 mAh.cm$^{-2}$. The electrolyte was prepared in a manner similar to that of Example 6 with a solution of 0.15 M.kg$^{-1}$ of Li(CF$_3$SO$_2$)$_2$N in the polar compound of Example 1 in a polypropylene porous separator of the Celgard® type. The generator was cycled over 500 cycles between 1.5 et 3.3 V á C/4 while maintaining a ratio of charge and discharges capacities equal to 1 and a use rate of 80%.

EXAMPLE 8

An electrochemical generator of the supercapacitor type is prepared with 2 symetrical composite electrodes of high surface area carbon (680 m$^2$.g$^{-1}$) and nickel fibres on a nickel support, and bound by a vinylidene fluoride—hexafluoropropene copolymer. The electrolyte comprises 75% by wieght of a gel of a molar solution of tetraethylammonium fluorosulfonimide (C$_2$H$_5$)$_4$N[(CF$_3$SO$_2$)$_2$N] in the same polymer. The system capacity is 1.2 F.g$^{-1}$ over 12 000 cycles performed between 0 and 2.5 V.

EXAMPLE 9

A polymer electrolyte is prepared by plasticizing an ethylene oxide—allylglycidyl ether copolymer containing the lithium salt of dimethylarninosulfonyl-trifluoromethane-sulfonimide Li[(CH$_3$)$_2$SO$_2$NSO$_2$CF$_3$] with a ratio oxygen from the ether functions of the polymer to lithium of 14:1 with the polar compound of Example 5 with a weight ratio 65:35. This electrolyte has a conductivity of 10$^{-4}$ Scm$^{-1}$ at 25° C. and an electrochemical stability range of 0 to 4V vs. Li$^+$/Li°. This electrolyte can be reticulated by a free radical source to give elastomers with good mechanical properties.

While the invention has been described in connection with specific embodiments thereof, it will be understood that it is capable of further modifications and this application is intended to cover any variations, uses or adaptations of the invention following, in general, the principles of the invention and including such departures from the present description as come within known or customary practice within the art to which the invention pertains, and as may be applied to the essential features hereinbefore set forth, and as follows in the scope of the appended claims.

What is claimed is:

1. An aprotic polar compound having solvent properties, and of the general formula:

wherein

X=C or SO;

Z=O, NSO$^2$NR$^3$R$^4$ or NCN;

R$^1$ and R$^2$ are the same or different and are C$_{1-18}$ alkyl, C$_{1-18}$ oxaalkyl, C$_{1-18}$ alkylene or C$_{1-18}$ oxaalkylene;

R$^3$ to R$^4$ are the same or different and are C$_{1-18}$ alkyl or C$_{1-18}$ oxaalkyl;

R$^7$ is R$_F$, R$_F$CH$_2$O—, (R$_F$)$_2$CHO, or (R$_F$CH$_2$)$_2$N—;

R$_F$ is a fluorine atom, C$_{1-4}$ alkyl, C$_{1-4}$ oxaalkyl C$_{1-4}$ azaalkyl, wherein C$_{1-4}$ alkyl, C$_{1-4}$ oxaalkyl and C$_{1-4}$ azaalkyl are each essentially fluorinated.

2. An electrolytic composition comprising at least one polar compound according to claim 1, a salt soluble in said compound having an anion with a delocalized charge, and at least one polymer.

3. An electrolytic composition according to claim 2, wherein the salt comprises I$^-$, ClO$_4^-$, BF$_4^-$, PF$_6^-$, AsF$_6^-$, SbF$_6^-$, R$_F$SO$_3^-$, XSO$_2$NSO$_2$X'$^-$, (XSO$_2$)(X'SO$_2$)(Y)C$^-$, anionic derivatives of 4,5-dicyano-1,2,3-triazole, 3,5 -bis (R$_F$)-1,2,4-triazole, tricyanomethane, pentacyanocyclopentadiene and pentakis(trifluoromethyl)cyclopentadiene, R$_F$SO$_2$NCN$^-$, C(CN)$_3^-$, R$_F$SO$_2$C(CN)$_2^-$, and mixtures thereof, wherein X and X' comprise R$_F$, R$_F$CH$_2$O—, (R$_F$)$_2$CHO—, (R$_F$CH$_2$)$_2$N—, R$^8$, R$^9$R$^{10}$N—, with the proviso that at least one X or X' is R$_F$, R$_F$CH$_2$O—, (R$_F$)$_2$CHO—, or (R$_F$CH$_2$)$_2$N—;

Y=R$_F$, R$_F$SO$_2$ or CN;

R$_F$ is as defined above and can be part of a macromolecular chain; and

R$^8$ to R$^{10}$ are the same or different, and are C$_{1-8}$alkyl or C$_{1-18}$ oxaalkyl.

4. An electrolytic composition according to claim 3, wherein the cation includes alkaline metals, alkaline earth metals, and organic onium cations, comprising ammonium, imidazolium, sulfonium, phosphonium, oxonium or mixtures thereof.

5. An electrolytic composition according to claim 4, wherein the cation is at least partly lithium.

6. An electrolytic composition according to claim 2 further comprising a co-solvent.

7. An electrolytic composition according to claim 6, wherein the co-solvent is aprotic and polar, and comprises dialkyl ethers of ethylene glycol, diethylene glycol, triethylene glycol, polyethylene glycols; carbonic acid esters, γ-butyrolactone, nitriles, tricyanohexane, dimethyl formamide, N-methylpyrrolidinone, or mixtures thereof.

8. An electrolytic composition according to claim 7, wherein the polyethylene glycol mass is comprised between 400 and 2000.

9. An electrolytic composition according to claim 8, wherein at least one polymer is a polyelectrolyte comprising a macromolecular chain and having a delocalized anionic charge.

10. An electrolytic composition according to claim 7, wherein the composition is plasticized or in the form of a gel.

11. An electrolytic composition according to claim 2, wherein the polymer comprises monomer units derived from ethylene oxide, propylene oxide, epichlorohydrine, epifluorohydrine, trifluoroepoxypropane, acrylonitrile, methylmetacrylate, vinylidene fluoride, and N-vinylpyrolidinone, hexafluoropropene, either as homo- or copolymers, or mixtures thereof.

* * * * *

UNITED STATES PATENT AND TRADEMARK OFFICE
CERTIFICATE OF CORRECTION

PATENT NO.    : 6,296,973 B1
DATED         : October 2, 2001
INVENTOR(S)   : Michot et al.

It is certified that error appears in the above-identified patent and that said Letters Patent is hereby corrected as shown below:

<u>Title page,</u>
Item [73], the Assignee information should read:

-- [73] Assignees:  ACEP Inc., Montreal (CA); Centre National de la Recherche Scientifique, Paris (FR); Universite de Montreal, Montreal (CA) --

Signed and Sealed this

Sixth Day of May, 2003

JAMES E. ROGAN
*Director of the United States Patent and Trademark Office*